US005650438A

United States Patent [19]
Meier et al.

[11] Patent Number: 5,650,438
[45] Date of Patent: Jul. 22, 1997

[54] PROCESS FOR ACTIVATING REPRODUCTION IN SEASONAL BREEDING ANIMALS BY ADMINISTERING L-DIHYDROXYPHENYLALANINE (L-DOPA)

[75] Inventors: Albert H. Meier, Baton Rouge; John M. Wilson, Metairie, both of La.

[73] Assignee: The Board of Supervisors of Louisiana University and Agricultural and Mechanical College, Baton Rouge, La.

[21] Appl. No.: 463,728

[22] Filed: Jun. 5, 1995

Related U.S. Application Data

[63] Continuation of Ser. No. 949,874, filed as PCT/US91/04115, Jun. 11, 1991, abandoned, which is a continuation-in-part of Ser. No. 538,538, Jun. 13, 1990, abandoned.

[51] Int. Cl.$^6$ .......................... A61K 31/195; A61K 31/24
[52] U.S. Cl. ............................................. 514/567; 514/538
[58] Field of Search ...................... 514/567, 538

[56] References Cited

U.S. PATENT DOCUMENTS

| | | | |
|---|---|---|---|
| 3,462,536 | 8/1969 | Chemerda et al. | 514/538 |
| 4,241,082 | 12/1980 | Baba et al. | 514/538 |

FOREIGN PATENT DOCUMENTS

| | | |
|---|---|---|
| 1518726 | 7/1978 | United Kingdom . |

OTHER PUBLICATIONS

W. Haresign et al. *Endocrine Control of Reproduction in the Ewe,* Sheep Production, pp. 353–379 (1974).
J.F. Roche et al. *Effects of Maltonin on the Time of Onset of the Breeding Season in Different Breeds of Sheep,* Endocrine Causes of Seasonal and Lactational Anestrus in Farm Animals, 1984, pp. 55–65.
M.R. Jainudden et al. *Sheep and Goats,* Reproduction in Farm Animals, 1987, pp. 315–323.
Michael J. Aminoff, *Pharmacologic Management of Parkinsonims & Other Movement Disorders,* Basic and Clinical Pharmacology, pp. 306–314 (1976).
W.R. Allen, *Control of Oestrus and Ovulation in the Mare,* Control of Ovulation, pp. 453–468 (1971).
Suzanne Gaston, Abstract *Photoperiodic Controll of Hamster Testis,* Science, vol. 158, 1967.
T.d. Siopes et al. *The Cloacal Gland—and External Indicator of Testicular Development in Coturnix,* pp. 1225–1229 (1970).
E.L. Squires et al. *Effect of an oral Progestin on the Estrous Cycle and Fertility of Mares,* Journal of Animal Science, vol. 49, No. 3 (1979), pp. 729–735.
M.H. Stetson et al. *Termination of Photorefractoriness in Golden Hamsters—Photoperiodic Requirements,* J. Exp. Zool., 202, pp. 81–87 (1982).
J.J. Robinson et al. *The Use of Progestagens and Photoperiodism in Improving the Reproductive Rate of the Ewe,* Ann.Biol.anim.Bioch.Biophys., 1975, 15, pp. 345–352.

J.E. Robinson et al. *Photoperiodism in Japanese Quail: the Termination of Seasonal Breeding by Photorefractoriness,* Proc.R.Soc.Lond, B215, 1982, pp. 95–116.
B. Rusak, et al. *Testicular Responses to Photoperiod Are Blocked by Lesions of the Suprachiasmatic Nuclei in Golden Hamsters,* Biology of Reproduction 15, 1976 pp. 366–374.
L.J. Forman et al., *Maintenance by L–DOPA Treatment of Estrous Cycles and LH Response to Estrogen in Aging Female Rats,* Experimental Aging Research, vol. 6, No. 6, 1080 (1980).
A. Goodman Gilman et al., *The Pharmacological Basis of Therapeutics,* pp. 466–472 (1984).
Russel J. Reiter, *Pineal Control of a Seasonal Reproductive Rhythm in Male Golden Hamsters Exposed to Natural Daylight and Temperature,* Endo. 1973, vol. 92, No. 2, pp. 423–430.
Russel J. Reiter, *The Pineal and its Hormones in the Control of Reproduction in Mammals,* Endocrine Reviews, vol. 1, No. 2, 1980, pp. 109–131.
J.G. Nutt et al., *The "On–Off" Phenomenon in Parkinson's Disease,* The New England Journal of Medicine, Feb. 23, 1984, pp. 483–488.
Miller & Meier, "Circadian Neurotransmitter Activity Resets the Endogenous Annual Cycle in a Migratory Sparrow," Journal of Interdisciplinary Cycle Research, 1983, vol. 14, No. 2, pp. 85–94.
Miller & Meier, "Temporal Synergism of Neurotransmitter—Affecting Drug Influences Seasonal Conditions in Sparrows," Journal of Interdisciplinary Cycle Research, 1983, vol. 14, No. 1, pp. 75–84.
Emata, Meier & Spieler, "Temporal Variations in Gonadal and Body Fat Responses to Daily Injections of 5–Hydroxytryptophan (5–HTP) and Dihydroxyphenylalanine (DOPA) in the Gulf Killifish, *Fundulus grandis,*" The Journal of Experimental Zoology, 1985, 233:29–34.
Kledzik and Meites, "Reinitiation of Estrous Cycles in Light–Induced Constant Estrous Female Rats by Drugs (38233)," Proceedings of the Society for Experimental Biology and Medicine, 1974, 146, pp. 989–992.
Wilson and Meier, "Resetting the Annual Cycle with Timed Daily Injections of 5–Hydroxytryptophan and L–Dihydroxyphenylalanine in Syrian Hamsters", Chronobiology International, vol. 6, No. 2 pp. 113–121, 1989.
Chaturvedi and Bhatt, "The Effect of Different Temporal Relationships of 5–Hydroxytryptophan (5–HTP) and L–dihydroxyphenylalanine (L–DOPA) on Reproductive and Metabolic Responses of Migratory Red–Headed Bunting "(*Emberiza bruniceps*), J. Interdiscipl. Cycle Res., 1990, vol. 21, No. 2, pp. 129–139.
Ward, S.J. et al. (1987) Out of Season Breeding in Adult Suffolk Ewes Following Light and Melatonin Treatment. In: British Society of Animal Reproduction 44(3):485.

*Primary Examiner*—Kevin E. Weddington
*Attorney, Agent, or Firm*—Darby & Darby

[57] ABSTRACT

A process is provided for activating reproduction in seasonal breeding vertebrates during normally non-reproductive seasons by administering L-dihydroxyphenylalanine (L-DOPA), thereby increasing the level of L-DOPA in the vertebrate's bloodstream to a reproductively active level. An effective amount of 5-HTP can also be injected into the vertebrate followed, an effective period of time later, with an injection of an effective amount of L-DOPA.

14 Claims, No Drawings

PROCESS FOR ACTIVATING REPRODUCTION IN SEASONAL BREEDING ANIMALS BY ADMINISTERING L-DIHYDROXYPHENYLALANINE (L-DOPA)

This is a continuation of application Ser. No. 07/949,874, filed Nov. 12, 1992, now abandoned which is the U.S. national phase of International Application No. PCT/US91/04115, filed Jun. 11, 1991, which is a continuation-in-part of Ser. No. 07/538,538, filed Jun. 13, 1990, now abandoned.

TECHNICAL FIELD

This invention relates to a process for causing seasonal breeding animals to breed during a normally non-reproductive season by administering L-dihydroxyphenylalanine (L-DOPA) alone, or an injection of 5-hydroxytryptophan (5-HTP) followed by an injection of L-DOPA an effective period of time after.

BACKGROUND ART

Seasonal breeding is a common reproductive strategy among vertebrate species and is a natural process that enables the young to be raised during periods of greatest survivability. Seasonal breeding is characterized by recurring annual periods of fertility and infertility that are a result of a natural endogenous physiological mechanism. Environmental factors such as photoperiod, temperature and nutrition may slightly modify this mechanism, particularly in the respect that they help maintain appropriate timing of reproductive events during the year.

The endogenous physiological nature of seasonal breeding can be illustrated by an example. Many species of birds, including domestic turkeys and some species of chickens become fertile and breed in the spring under the stimulatory influence of long daylengths. However, in summer, even though daylengths are still long, reproductive activity declines and the birds become infertile. This is a natural mechanism preventing birth of young too late in the year to preclude winter survival. The mechanism for the summer decline in fertility is endogenous in that these birds are no longer responsive to the stimulatory influences of long daylengths as they had been in spring. Some other economically important seasonal breeders include: sheep, mink, goats and deer, naturally fertile in fall under the influence of short daylengths then becoming spontaneously infertile in mid-late winter.

Furthermore, the reproductive system of Syrian hamsters is inhibited by short daylengths in fall but not in late winter and early spring. The basis for sensitivity and refractoriness to daylengths is unknown but probably involves the neuroendocrine system.

Resetting the endogenous seasonal mechanism would have clear economic benefits by increasing the numbers of animals that could be produced.

Applicants' laboratory has been researching seasonality in fish, birds and mammals for over 20 years. This research suggested that mechanisms controlling the seasonality are similar in all vertebrate animals and involves changes in brain neurotransmitter activities.

Recently, Meier and Wilson (the inventors) discovered that L-dihydroxyphenylalanine (L-DOPA) has a vital role in seasonality. L-DOPA was found to be present in hypothalamic areas of the brain (anterior hypothalamic nuclei) that regulate reproductive activity in much higher concentrations in reproductively stimulated than in reproductively regressed hamsters. Blood concentrations of L-DOPA were also greater in reproductively active hamsters than in the inactive animals. Plasma L-DOPA concentrations in reproductively inactive hamsters have been found to be about 0.62 ug/ml, while the level in reproductively active hamsters is in the range of 0.85 to 1.09 ug/ml.

It has been observed that 40–50% of an oral dose of L-DOPA (25 mg/kg, dog) is absorbed from the digestive tract (Aminoff, 1987). However, the absorption of L-DOPA is highly dependent upon the frequency of gastric emptying, the protein content of the diet and whether taken with a meal (Nutt et al., 1987). Peak plasma concentrations of L-DOPA are attained within 1–2 hours. After 8 hours, 66% of an oral dose of L-DOPA can be recovered in the urine as homovanillic acid and dihydroxyphenylacetic acid (Aminoff, 1987). The half-life of L-DOPA in the blood stream is 1–3 hours (Gilman et al., 1985).

Instead of an oral dose, L-DOPA may be administered by time release subcutaneous implant or by injection, both of which are approximately three times more efficient than an oral dose.

L-DOPA, a catecholamine precursor, has been used for treatment of degenerative conditions brought on by old age. For years L-DOPA has been used to treat Parkinson's disease, a disease of later life characterized by rhythmic tremors and muscular rigidity caused by degeneration of the basal ganglia of the brain. Additionally, treatment with L-DOPA has been found to enhance response to estrogen feedback and maintain estrous cycles in old female rats in various stages of reproductive decline (Forman et al., 1980). Furthermore, in U.S. Pat. No. 4,241,082, Baba et al. teach the use of L-DOPA for promoting the reproductive ability in domestic animals suffering from reproductive disorders during their breeding season. It does not suggest that L-DOPA can be used to stimulate the reproduction of seasonally reproductively inactive animals, which is not a disorder. It is merely part of the normal breeding cycle of the animal.

The present invention is based on the hypothesis that the high levels of L-DOPA in the blood and brain have a causal role in establishing and maintaining reproductive readiness.

There is presently no method known to applicants that compares with the present invention for producing reproductive activity in animals during a normally non-reproductive season of the year, which is not brought on by any disorder. Present methodology involves artificial manipulation of the daily photoperiod or injections of reproductive hormones. For example, short daylengths in summer can cause premature breeding in sheep that otherwise occurs during the fall (Jainudeen and Hafez, 1987). Recently, melatonin, a pineal gland hormone produced in greater amounts during short daylength exposure, has been employed to initiate early breeding. (Roche et al., 1985; Ward and Williams, 1987). Artificially lengthening the daylength at the end of the seasonal anestrous period in mares may initiate early estrous cycling (Allen, 1978). These methods are expensive and while they produce young at a different season, they do not increase the total number that can be produced during a year. Injections of reproductive hormones, such as gonadotropin releasing hormone and progestogens, have also been used to develop reproductive readiness in several vertebrate animals, such as sheep, horses, swine, and poultry (Robinson et al., 1975; McGlothlin et al., 1979; Haresign, et al., 1983). This method is labor intensive and uneconomical or unfeasible in most instances.

The following is a list of the relevant prior art references cited herein:

Allen, W. R. 1978. Control of estrous and ovulation in the mare. In: Control of Ovulation (D. B. Crighton, G. R. Foxcroft, N. B. Haynes, G. E. Lamming, eds.), Butterworths, London.

Aminoff, M. J. 1987. Pharmacological management of Parkinsonism and other movement disorders. In: Basic and Clinical Pharmacology (B. G. Katzung, ed.), Appleton and Lange, Norwolk, Ct. pp. 306–309.

Forman, L. J., W. E. Sonntag, N. Miki, and J. Meites 1980. Maintenance by L-DOPA treatment of estrous cycles and LH response to estrogen in aging female rats. Exp. Aging Res. 6:547.

Gaston, S. and M. Menaker 1967. Photoperiodic control of hamster testis. Science 158:925.

Gilman, A. G., L. Goodman and A1 Gilman 1985. Pharmacological Basis of Therapeutics. 7th Ed., MacMillan Publ., N.Y.

Haresign, W., B. J. McLoed and G. M. Webster 1983. Endocrine control of reproduction in the ewe. In: Sheep Production (W. Haresign, ed.). Butterworth, London. pp. 353–379.

Jainudeen, M. R. and E. S. E. Hafez 1987 (Reproductive cycles of sheep and goats. In: Reproduction in Farm Animals (E. S. E. Hafez, ed.), 5th ed., Lea and Febiger, Philadelphia. pp. 315–323.

McGlothlin, D. E., E. L. Squires, W. B. Stevens and B. W. Pickett 1979. Effect of an oral progestin on the estrous cycle and fertility in mares. J. Anim. Sci. 4:729.

Nutt, J. G., W. R. Woodward, J. P. Hammerstal, J. H. Carter and J. L. Anderson 1987. The on-off phenomenon in Parkinson's disease: Relation to levodopa absorption and transport. New Engl. J. Med. 310:483.

Reiter, R. J. 1973. Pineal control of the seasonal reproductive rhythm in male golden hamsters exposed to natural daylengths and temperature. Endocrinology 92:423.

Reiter, R. J. 1981. The pineal and its hormones in the control of reproduction in mammals. Endocrine Rev. 1:109.

Robinson, J. E. and B. K. Follett 1982. Photoperiodism in Japanese quail: The termination of seasonal breeding by photorefractoriness. Proc. R. Soc. London, Ser. B. 215:95.

Robinson, J. J., C. Fraser and I. McHatter 1975. Use of progestogens and photoperiodism in improving the reproductive rate of the ewe. Ann. Biol. Anim. Biochem. Biophys. 15:345.

Roche, J. F., J.P. Hanrahan, J. F. Quicke and E. Ramayne 1985. Effect of melatonin on time of onset of breeding season in different breeds of sheep. In: Endocrine Causes of Seasonal and Lactational Anestrous in Farm Animals (F. Ellendorf, ed.), Martinus Nijhoff, Dordrecht, pp. 55–64.

Rusak, B. and L. P. Morin 1967. Testicular responses to photoperiod are blocked by lesions of the suprachiasmatic nuclei of golden hamsters. Biol. Reprod. 15:366.

Siopes, T. D. and W. O. Wilson 1975. The cloacal gland: An external indication of testicular development in Coturnix. Poult. Sci. 54:1225.

Stetson, M. H., M. Watson-Whitmyre and K. S. Matt. 1977. Termination of photorefractoriness in the golden hamster: Photoperiodic requirements. J. Exp. Zool. 202:81.

Ward, S. J. and H. L. Williams 1987. Out-of-season breeding in adult Suffolk ewes following light and melatonin treatment. In: British Society of Animal Production. Winter Meeting, 23–24 Mar. 1987. Program and Summaries, Paper No. 88.

U.S. Pat. No. 4,241,082 issued on Dec. 23, 1980 to Yoshihiko Baba and Hiroyoshi Horikoshi, entitled "Agents for Promoting Reproductive Ability of Domestic Animals."

Therefore, one object of the invention is to provide a process to alter seasonality in seasonal breeding vertebrates.

Another object of this invention is to provide a process to convert vertebrates from a reproductively inactive to a reproductively active state.

Another object of this invention is to provide a process to maintain vertebrates in a reproductively active state during photoperiodic conditions which would otherwise cause inhibition of reproductive activity.

Another object of this invention is to provide a process to shift seasonality which is safe and easy to administer.

Another object of this invention is to use the prevailing photoperiodic conditions to stimulate reproductive activity.

Still another object of this invention is to provide a process to inhibit the depletion of L-DOPA in a vertebrate's bloodstream.

DISCLOSURE OF INVENTION

Accordingly, a process is provided for activating reproductive activity in seasonal breeding vertebrates during a normally reproductively inactive season by administering L-DOPA to a vertebrate to increase the level of L-DOPA in said vertebrate's bloodstream above a reproductively inactive level. Treatment for approximately seven days is recommended to induce reproductive activity. Alternatively, existing reproductive activity can be maintained by administering L-DOPA.

Also in accordance with the present invention is a process for activating reproductive activity in seasonal breeding animals during a normally inactive season by first injecting the vertebrate with an effective amount of 5-HTP followed by an injection of an effective amount of L-DOPA at an effective period of time later.

BEST MODE FOR CARRYING OUT THE INVENTION

Without limiting the scope of the invention, the best mode for carrying out the invention will be set forth.

Introducing L-DOPA into the bloodstream of seasonal breeding animals has been found to stimulate reproductive activity in seasonally reproductively inactive animals. A preferred method is to treat an animal's food with L-DOPA. Alternative methods for providing sustained increased levels of L-DOPA in an animal's bloodstream may be employed. For example, those with skill in the art may use subcutaneous time release implants or multiple injections.

Another preferred method is to first inject the animal with an effective amount of 5-HTP followed by an injection of an effective amount of L-DOPA at an effective period of time later. By effective amount, we mean from at least that amount which will stimulate reproduction in the animal up to that amount which will have adverse effects or to toxicity levels. Generally this amount will be about 0.1 to 200 mg/kg of body weight, preferably about 0.5 to 25 mg/kg of body weight.

The period of time between injections of 5-HTP and L-DOPA will be an effective period of time. That is, at a period of time at which the injection of L-DOPA will interact synergistically with the earlier injection of 5-HTP. The period of time will vary somewhat from specie to specie. For example, in most animals, the period of time will be from about 8 to 16 hours, preferably about 10 to 14 hours, and more preferably about 11 to 13 hours. In fish, the effective period between injections appears to be from about 16 to 24 hours, preferably from about 18 to 22 hours, and more preferably from about 19 to 21 hours. The precise period of time between injections of 5-HTP and L-DOPA can easily be determined by those having skill in the art by a few routine experiments. Exhaustive experimentation is not needed.

The concentration of L-DOPA in the blood is greatest when an animal is reproductively active and decreases to a reproductively inactive level when seasonal regression occurs. As an alternative to administering only L-DOPA to maintain increased levels of L-DOPA in the blood, drugs which inhibit the degradation of L-DOPA may also be administered. Examples of such drugs are carbidopa and benserazide which have been used in conjunction with L-DOPA in the treatment of Parkinson's disease. By using the aforementioned inhibitors the amount of L-DOPA required to be administered can be reduced or eliminated resulting in a substantial economic savings.

Other methods of maintaining reproductively active levels of L-DOPA or increasing the level of L-DOPA in the bloodstream are intended to be included within the scope of applicants' invention. For example, food containing naturally occurring L-DOPA or drugs which stimulate L-DOPA synthesis may be administered. The root of applicants' invention is that the level of L-DOPA in an animal may be artificially manipulated to induce or maintain reproductive activity.

As used herein the term L-dihydroxyphenylalanine (L-DOPA) is intended to include molecules containing substitutions in the chemical formula of L-DOPA not effecting the chemical activity and efficacy of the L-DOPA molecule for stimulating reproduction.

Also, as used herein, the term 5-hydroxytryptophan (5-HTP) is intended to include molecules containing substitutions in the chemical formula of 5-HTP not effecting the chemical activity and efficacy of the 5-HTP molecule for stimulating reproduction.

tinuous exposure to short daylengths. Afterward, the reproductive system recrudesces even while the animals are held on short daylengths. Re-establishment of scotosensitivity requires 7–11 weeks exposure to long daylengths (>12.5 hours light) (Stetson, et al., 1977).

Experiment 1

Scotosensitive male hamsters (100–110 g body weight) that had been raised on long daylengths (LD 14:10) were placed on short daylengths (LD 10:14). After 6 weeks of short daylengths, half of the hamsters were provided L-DOPA (50 mg/hamster/day) in their feed. After 8 more weeks, L-DOPA feeding was stopped and the males were mated with reproductively active control females for a period (nine days) encompassing two estrous cycles. Male hamsters without L-DOPA supplements in the feed were similarly mated with active females. The L-DOPA-fed males produced seven pregnancies in 11 females. This percentage (64%) compares favorably with that expected in fully developed and naturally reproductively active male and female hamsters under the best of conditions (70–80% success). The number of progeny (5–13) for each pregnancy was also normal. On the other hand, the males not treated with L-DOPA were completely ineffective as expected in producing pregnancies. Of eleven females employed, none became pregnant.

The external dimensions of the left testes were also greater in the L-DOPA-treated than in the control males (Table 1). Although the testis index of control males declined to inactive levels, the testes of L-DOPA-fed males remained at active levels throughout the period of L-DOPA feeding. Testes indices of 1.6–2.0 are typical levels for naturally reproductively active hamsters (Rusak and Morin, 1976).

TABLE 1

L-DOPA Feeding Restores Reproductive Capacity in Scotosensitive Hamsters
TESTIS INDEX

| | | | After Treatment | | | |
|---|---|---|---|---|---|---|
| | n | Before Treatment | 1 week | 4 weeks | 6 weeks | 8 weeks |
| Controls | 7 | 1.51 ± 0.07 | 1.30 ± 0.11 | 1.06 ± 0.09 | 1.30 ± 0.11 | 1.12 ± 0.04 |
| L-DOPA | 8 | 1.51 ± 0.08 | 1.58 ± 0.06 | 1.66 ± 0.08 | 1.60 ± 0.08 | 1.80 ± 0.09 |

Length (mm) × Width (mm) of left testis - body weight.

The annual reproductive cycle of the Syrian hamster is divisible into two parts by the manner of response to short daylengths (<12.5 hours light) (Gaston and Menaker, 1967); Reiter, 1973). Short daylengths are inhibitory to the reproductive system in scotosensitive but not in scotorefractory animals. Long daylengths permit reproductive activity of hamsters in both scotosensitive and scotorefractory conditions (Reiter, 1981). In animals held under natural seasonal changes in daylengths hamsters are scotosensitive in summer, fall and early winter and scotorefractory in late winter and spring. Conversion from scotosensitive to scotorefractory conditions requires about 20 weeks of con- Experiment 2

Male Syrian hamsters were raised on long daylengths for 14 weeks to establish scotosensitivity, then transferred to short daylengths. Upon transfer to short daylengths ⅓ of the hamsters were provided L-DOPA (25 mg/hamster/day) in the diet and another ⅓ were provided carbidopa (0.5 mg/hamster/day) in the diet. After 8–10 weeks of maintenance on short daylengths, the reproductive organs of control hamsters were completely regressed (Table 2). However, the testis indices remained at stimulated levels in L-DOPA-fed hamsters. Carbidopa was effective at inhibiting the rate at which the hamsters returned to a regressed state.

TABLE 2

L-DOPA Feeding Maintains Reproductive Capacity of Scotosensitive Male Hamsters.
TESTIS INDEX

| | n | Initial | 2 | 5 | Weeks of Treatment 8 | 10* | 12* |
|---|---|---|---|---|---|---|---|
| Control | 6 | 2.71 ± 0.05 | 2.05 ± 0.06 | 1.74 ± 0.11 | 1.25 ± 0.04 | 1.06 ± 0.05 | 1.05 ± 0.0 |
| Carbidopa | 6 | 2.79 ± 0.06 | 2.47 ± 0.12 | 1.89 ± 0.13 | 1.24 ± 0.09 | 1.39 ± 0.12 | 1.41 ± 0.1 |
| M. L-DOPA | 8 | 2.58 ± 0.09 | 2.64 ± 0.07 | 2.55 ± 0.14 | 2.71 ± 0.20 | 1.86 ± 0.22 | 1.89 ± 0.1 |

*Males receiving L-DOPA were separated after fighting

Experiment 3

Female scotosensitive hamsters that had been raised on long daylengths and were undergoing normal estrous cycling were separated into four groups of six hamsters each. After transfer to short daylengths, 3 of the groups of hamsters were treated with low (5 mg/hamsters/day), medium (25 mg/hamster/day) and high (50 mg/hamster/day) doses of L-DOPA. Estrous cycling was monitored daily throughout the treatment period. After 9 weeks on short daylengths 66–84% of the L-DOPA treated hamsters were still estrous cycling (Table 3). Only 33% of control hamsters were reproductively active.

TABLE 3

L-DOPA Feeding Maintains Estrous Cycling in
Scotosensitive Female Hamsters
ESTROUS CYCLING

| | Initial | 2 | Weeks of Treatment 4 | 6 | 9 |
|---|---|---|---|---|---|
| U | 6/6 | 6/6 | 5/6 | 4/6 | 2/6 |
| L. L-DOPA | 6/6 | 6/6 | 5/6 | 4/6 | 4/6 |
| M. L-DOPA | 6/6 | 6/6 | 5/6 | 5/6 | 4/6 |
| H. L-DOPA | 6/6 | 6/6 | 6/6 | 6/6 | 5/6 |

Experiment 4

The effects of L-DOPA feeding on reproductive responsiveness to daylength was also tested in Japanese quail. Photosensitive quail are reproductively stimulated by daylengths greater than 12 hours but become photorefractory after eight weeks of such daylengths so that the reproductive system regresses on daylengths less than about 15 hours (Robinson and Follett, 1983). Following development of photorefractoriness, male quail were provided control or L-DOPA-supplemented (25 mg/quail/day) food for 10 days. Both groups were then transferred to 13.5 hour daylengths. After six weeks, normal-fed male quail became reproductively inactive as expected of refractory quail (Table 4). However, those quail that received L-DOPA supplements remained reproductively stimulated as indicated by the size of the cloacal glands (Siopes and Wilson, 1975).

TABLE 4

| | | CLOACAL GLAND VOLUME (CM ) | | | |
|---|---|---|---|---|---|
| | | | After Treatment (Days) | | |
| | Before Treatment Long Daylengths | 10 | 30 LD 13.5:10.5 | 45 | 52 |
| Control | 1.02 ± 0.04 | 1.21 ± 0.10 | 0.55 ± 0.11 | 0.47 ± 0.12 | 0.37 ± 0.12 |
| L-DOPA | 1.24 ± 0.09 | 1.80 ± 0.10 | 1.45 ± 0.29 | 1.48 ± 0.28 | 1.45 ± 0.28 |

As previously mentioned, when quail are photosensitive they are reproductively stimulated by light:dark conditions having a ratio greater than 1, i.e. greater than 12 hours of daylight. Even through the quail in the above experiment were in a photorefractory state prior to treatment, they were converted to a photosensitive state by the administration of L-DOPA. The exact mechanism by which L-DOPA works is not completely understood. However, it appears that variations of L-DOPA in the anterior hypothalamic nuclei may account for changes in reproductive readiness. It is believed that L-DOPA treatment to activate reproductivity is best performed at a time when light:dark conditions are analogous to a time when reproductive activity is naturally stimulated. For example, a light:dark ratio of 13.5:10.5 may be stimulatory in early summer but not in late summer. In the foregoing case, applicants' invention may be used to induce reproductive activity in late summer.

Experiment 5

Male hamsters undergoing reproductive regression on short daylengths were injected with: (a) 5-HTP and L-DOPA at the same time; (b) 5-HTP then 12 hours later with L-DOPA; (c) 5-HTP only; (d) L-DOPA only; and (e) only a saline solution. The testes were weighed and it was found that the injection with 5-HTP followed 12 hours later with an injection of L-DOPA substantially increased the weight of the testes. When 5-HTP and L-DOPA were injected at the same time, the testes were reduced in weight when compared to a saline only injection. Injections of 5-HTP alone and L-DOPA alone showed little, if any, effect on testes weight over the saline only injection.

Experiment 6

Male and female hamsters that were undergoing reproductive regression on short daylengths (LD 10:14) were given nine daily injections of 5-HTP (25 mg/kg body weight in 0.9% saline) and L-DOPA (50 mg/kg body weight in 0.9% saline) of saline in 0- or 12-h relationships. Following the last day of injections, hamsters were maintained for six more weeks on short daylengths, then tested for mating success with fully reproductively active members of the opposite sex. The results are shown in Tables 5 and 6 below.

TABLE 5

Testis Index and Mating Success of Scotosensitive
Male Hamsters Given 9 Daily Injections of 5-HTP and DOPA
and Maintained on Short Daylenghts

| Treatment | Testes Index Initial | Final | Mating Success |
|---|---|---|---|
| 5-HTP:DOPA | | | |
| 0 hr | 2.45 ± 0.21 | 1.21 ± 0.17 | 2/7 |
| 12 hr | 2.56 ± 0.09 | 2.34 ± 0.20 | 7/8 |
| Saline | | | |
| 0 hr | 2.62 ± 0.29 | 1.42 ± 0.11 | 0/6 |
| 12 hr | 2.71 ± 0.31 | 1.71 ± 0.16 | 2/8 |

TABLE 6

Estrous Cycling and Mating Success of Scotosensitive
Female Hamsters Given 9 Daily Injections of 5-HTP and DOPA
and Maintained on Short Daylenghts

| Treatment | Estrous Cycling Initial | Final | Mating Success |
|---|---|---|---|
| 5-HTP:DOPA | | | |
| 0 hr | 7/7 | 2/7 | 2/7 |
| 12 hr | 9/9 | 8/9 | 7/9 |
| Saline | | | |
| 0 hr | 6/6 | 0/6 | 0/6 |
| 12 hr | 6/6 | 2/6 | 2/6 |

The experiments present herein were performed on small vertebrates, less than 10 kg. All of the evidence indicates that the treatment process will be equally successful with larger vertebrates. Experience has shown that because the metabolism of large vertebrates is slower, less L-DOPA is required for treatment. L-DOPA treatment levels approximately 1/3 of those provided to small vertebrates may be efficacious in the treatment of larger vertebrates.

The length of the treatment period required to induce reproductive activity in reproductively inactive vertebrates depends on the particular species and the seasonal status of the individual. Some species, such as migratory birds, experience significant regression of reproductive activity during seasonal reproductively inactive periods. Other species, while dormant during reproductively inactive periods, may be easily stimulated to induce reproductive activity. An animal which has only recently entered a reproductively inactive period would be stimulated to a reproductively active state easier than one which was fully regressed. Because of the variations between species and status of the individuals within a seasonal cycle, it is difficult to predict the time required to induce reproductive activity with any degree of accuracy. After numerous experiments the following general observations may be made. Behavioral and physical changes in reproductive indices can be detected as early as one week after treatment with L-DOPA, and even shorter periods of time with injections of 5-HTP and L-DOPA. Increased levels of L-DOPA persist following a daily treatment making treatment on alternate days possible.

In addition to the experiments done on mammals and avian species, the L-DOPA level in fish with regard to sexual activity has been monitored. The results correspond to those of warm blooded animals, i.e. the blood level of L-DOPA increases when fish are in a reproductively active state, and decreases when they are in a reproductively inactive 'state. Therefore, all indications would be that the same procedures described above will be equally effective with regard to fish. This was not found to be the case when L-DOPA was used alone. Only when the fish were first injected with an effective amount of 5-HTP followed by an injection of an effective amount of L-DOPA were the fish stimulated to reproduce during a normally reproductively inactive state.

There are, of course, many obvious alternate embodiments and modifications of this invention which are intended to be included within the scope of the following claims.

What is claimed is:

1. A process for treating a vertebrate in a reproductively active state and having L-DOPA in the bloodstream at a reproductive activity level to prevent seasonal regression of said vertebrate to a reproductively inactive state, which comprises administering an effective amount of L-dihydroxyphenylalanine (L-DOPA) to said vertebrate for maintaining at least said reproductive activity level of L-DOPA in said vertebrate's bloodstream for a period of time sufficient for said vertebrate to breed, wherein said vertebrate is a mammal or a bird.

2. A process according to claim 1, further comprising the step of administering carbidopa to said vertebrate in an amount sufficient to inhibit degradation of L-DOPA with said vertebrate's system.

3. A process according to claim 1, wherein said effective amount comprises five milligrams of L-DOPA per kilogram of body weight.

4. A process according to claim 1 wherein said effective amount comprises between 5 milligrams and 210 milligrams of L-DOPA per kilogram of body weight per day.

5. A process according to claim 1, wherein said effective amount of L-DOPA is administered orally, by subcutaneous implant or injection.

6. A process for activating reproductive activity in a seasonally regressed, reproductively inactive vertebrate having L-DOPA in its bloodstream at a level below the reproductive activity level, comprising the step of administering an effective amount of L-dihydroxyphenylalanine (L-DOPA) to said vertebrate for increasing said L-DOPA level in said vertebrate's bloodstream to at least said reproductive activity level for a sufficient period of time for said vertebrate to breed, wherein said vertebrate is a mammal or bird.

7. A process according to claim 6, wherein said vertebrate has a seasonal breeding cycle and said L-DOPA is administered under seasonal conditions not conducive to reproductive activity.

8. A process according to claim 7, further comprising the step of administering carbidopa to said vertebrate in an amount sufficient to inhibit degradation of L-DOPA within said vertebrate's system.

9. A process according to claim 7, wherein said effective amount comprises 5 milligrams of L-DOPA per kilogram of body weight.

10. A process according to claim 7, wherein said effective amount comprises between 5 milligrams and 210 milligrams of L-DOPA per kilogram of body weight per day.

11. A process according to claim 10, which comprises administering said L-DOPA for at least eight days within a two week period.

12. A process according to claim 7, which comprises increasing said level of L-DOPA in said vertebrate's bloodstream to 35% above a reproductively inactive level.

13. A process for treating a vertebrate in a reproductively active state and having a reproductive activity level of L-DOPA in its bloodstream to prevent seasonal regression of said vertebrate to a reproductively inactive state which comprises administering an effective amount of carbidopa to said vertebrate for maintaining the amount of L-dihydroxyphenylalanine (L-DOPA) in said vertebrate's bloodstream at said reproductive activity level for a period of time sufficient for said vertebrate to breed, wherein said vertebrate is a mammal or a bird.

14. A process for treating a vertebrate in a reproductively active state and having a reproductive activity level of L-DOPA in its bloodstream to prevent seasonal regression of said vertebrate to a reproductively inactive state which comprises administering an effective amount of carbidopa to said vertebrate for maintaining the amount of L-dihydroxyphenylalanine (L-DOPA) in said vertebrate's bloodstream at said reproductive activity level for a period of time sufficient for said vertebrate to breed, wherein said vertebrate is a mammal or a bird.

* * * * *